5,116,942

United States Patent [19]
Inoue et al.

[11] Patent Number: 5,116,942
[45] Date of Patent: May 26, 1992

[54] PROTEIN HAVING AN INFLAMMATORY PHOSPHOLIPASE $A_2$ INHIBITORY ACTIVITY

[75] Inventors: Keizo Inoue; Atsushi Imaizumi; Takashi Kamimura; Yorimasa Suwa; Masahiro Okada; Yoji Suzuki; Ichiro Kudo, all of Tokyo, Japan

[73] Assignee: Teijin Limited, Osaka, Japan

[21] Appl. No.: 295,724

[22] PCT Filed: Mar. 30, 1988

[86] PCT No.: PCT/JP88/00318
§ 371 Date: Dec. 2, 1988
§ 102(e) Date: Dec. 2, 1988

[87] PCT Pub. No.: WO88/07552
PCT Pub. Date: Oct. 6, 1988

[30] Foreign Application Priority Data
Apr. 2, 1987 [JP] Japan ................. 62-79693

[51] Int. Cl.$^5$ ................. C07K 15/06; A61K 37/64
[52] U.S. Cl. ................. 530/350; 514/21; 435/69.2; 930/250
[58] Field of Search ................. 530/350; 514/21; 435/69.2; 930/250

[56] References Cited

U.S. PATENT DOCUMENTS

| | | | |
|---|---|---|---|
| 4,810,780 | 3/1989 | Imaizumi et al. | 530/350 |
| 4,874,743 | 10/1989 | Wallner et al. | 514/12 |
| 4,879,224 | 11/1989 | Wallner et al. | 435/235 |
| 4,937,324 | 6/1989 | Fujikawa et al. | 530/397 |

FOREIGN PATENT DOCUMENTS

| | | |
|---|---|---|
| 213916 | 4/1987 | European Pat. Off. |
| 8604094 | 2/1986 | World Int. Prop. O. |
| 8606100 | 10/1986 | World Int. Prop. O. |

OTHER PUBLICATIONS

Blackwell et al. (1980) Nature 287 147–149.
Repinsky et al. (1986) J. Biol. Chem. 261(9) 4239–4246.
Repinsky et al. (1988) J. Biol. Chem. 263(22):10799–10811.
Blackwell et al. (1982) 76:185–194.
Chem Abstr. 104:82112r (Flower (1985) Agents Actions 17(3-4) 255–262) Abstract.
Chem. Abstr. 100:62061n (Rothhut et al. (1983) abstract).
Chemical Abstracts, vol. 101, No. 104127s.
Chemical Abstracts, vol. 97, No. 66596h.
Aarsman et al., "Lipocortin Inhibition of Extracellular and Intracellular Phospholipases $A_2$ is Substrate Concentration Dependent", FEBS Lett., vol. 219, No. 1, pp. 176–180, Jul. 1987.
Y. Suwa, "Tanpakusitsu Kakusan Kouso", Proteins Nucleic Acids Enzymes, vol. 36, No. 3, pp. 333–341 (1991) translation of paragraph 5 on p. 138 and FIG. 1.
F. Davidson et al., "Inhibition of Phospholipase $A_2$ by Lipocortins and Calpactins", The Journal of Biological Chemistry, vol. 262, No. 4, pp. 1698–1705 (1987).
Y. Suwa et al., "Proteinaceous Inhibitors of Phospholipase $A_2$ Purfied from Inflammatory Sites in Rats", Proc. Natl. Acad. Sci. USA, vol. 87, pp. 2395–2399, Apr. 1990.
H. Chang et al., "Purification and Characterization of Extracellular Phospholipase $A_2$ from Peritoneal Cavity of Caseinate-Treated Rat", J. Biochem., vol. 102, No. 1, pp. 147–154 (1987).

Primary Examiner—Christine Nucker
Assistant Examiner—Kay K. Kim
Attorney, Agent, or Firm—Sughrue, Mion, Zinn, Macpeak & Seas

[57] ABSTRACT

Protein having inflammatory phospholipase $A_2$ inhibitory activity wherein said protein has a nature to be induced from cells by administration of glucocorticoid, for example, having a molecular weight of 40 K and the amino acid sequence from the N-terminal consisting of a N-terminal amino acid-Asp-Val-Pro-Ala-Ala-Asp-Leu-Ser-Asp-.

2 Claims, 6 Drawing Sheets

PROTEIN HAVING AN INFLAMMATORY PHOSPHOLIPASE A₂ INHIBITORY ACTIVITY

FIELD OF THE INVENTION

The present invention relates to protein having an inflammatory phospholipase A$_2$ (PLA$_2$) inhibitory activity. More particularly, this invention relates to protein which is induced from cells by the administration of glucocorticoid and has an inflammatory PLA$_2$ inhibitory activity.

BACKGROUND ART

Glucocorticoid is now widely used as one of the most efficacious medicines against various inflammatory diseases and allergic diseases inclusive of rheumatoid arthritis, lupus erythematosus, and bronchial asthma. The mechanism of its action is attributable to the anti-inflammatory action, anti-edematous action, and immunosuppressive action of glucocorticoid. Of these actions, the mode of anti-inflammatory action relates to the inhibition of the release of arachidonic acid, which is the precursor of prostaglandins or leukotriens regarded to be inflammatory mediators. A new theory has recently been put forward by Flower (Nature 278: 456 (1979)) that glucocorticoid suppresses the activity of PLA$_2$ which is a key enzyme to release arachidonic acid directly from the phospholipid. With regard to the action mechanism of glucocorticoid, it is understood that, when it enters into a cell, glucocorticoid is first bound to the receptor of the cell, then the resulting complex is translocated into the nucleus to activate the specific gene, finally inducing the synthesis of specific protein. Actually, Tsurufuji et al. have shown (Nature 280: 408 (1979)) that cycloheximide, an inhibitor of protein synthesis and actinomycin D, an inhibitor of mRNA synthesis, suppress the therapeutic effect of glucocorticoid against paw edema (experimental animal model of inflammation) caused by serotonin. Thus, it is suggestive from the above-mentioned results, that glucocorticoid displays its anti-inflammatory activity through the induction of the synthesis of PLA$_2$ inhibitory protein.

Attempts have hitherto been made by several groups to isolate such a protein whose synthesis is induced by glucocorticoid and that inhibits the activity of PLA$_2$ in vitro and suppresses the production of prostaglandin in vivo. In these attempts, porcine pancreas PLA$_2$ is used in their evaluation system. There are, however, another inflammatory PLA$_2$ having different properties from those of pancreas PLA$_2$ which has been generally regarded as playing a role of a digestive enzyme. Recently, Inoue et al [Biochemistry (written in Japanese) 58 (No. 8): 766 (1986)] have isolated and purified PLA$_2$ occurring in rat's peritoneal cavity and investigated its properties. They observed that the inoculation of 100 ng of purified enzyme into the skin of rat backs caused the rise in vascular permeability to leak out Evans blue which had been intravenously injected beforehand. In the meantime, PLA$_2$ originating from pancreas has not been confirmed to exhibit this activity. Further, Vadas et al reported that PLA$_2$ in the joints of rheumatoid arthritis is increased and that the purified enzyme does not react with the antibody of human pancreas PLA$_2$ (J. Biochem. 100, 1297–1030, 1986). Thus, the PLA$_2$ originating from pancreas differs from the inflammatory PLA$_2$ in the primary and tertiary structures and their roles in vivo are distinctly different from each other.

DISCLOSURE OF THE INVENTION

Under such backgrounds, the present inventors have made intense search for proteins which specifically inhibiting the enzyme and reached the present invention. The protein according to the present invention is induced from a cell by the administration of glucocorticoid, and particularly preferable protein is purified from the peritoneal cavities after administration of glucocorticoid to a rat and has an inflammatory PLA$_2$-inhibitory activity, having a molecular weight of 40 K and an amino acid sequence from the N-terminal consisting of a N-terminal amino acid-Asp-Val-Pro-Ala-Ala-Asp-Leu-Ser-Asp-, or is purified from the peritoneal cavities after administration of glucocorticoid to a rat and has an inflammatory PLA$_2$-inhibitory activity, having a molecular weight of 35 K and an amino acid sequence from the N-terminal consisting of a N-terminal amino acid-Glu-Arg-Leu-Lys-His-Leu-Ile-Val-.

BEST MODE OF CARRYING OUT THE INVENTION

Figure 1:
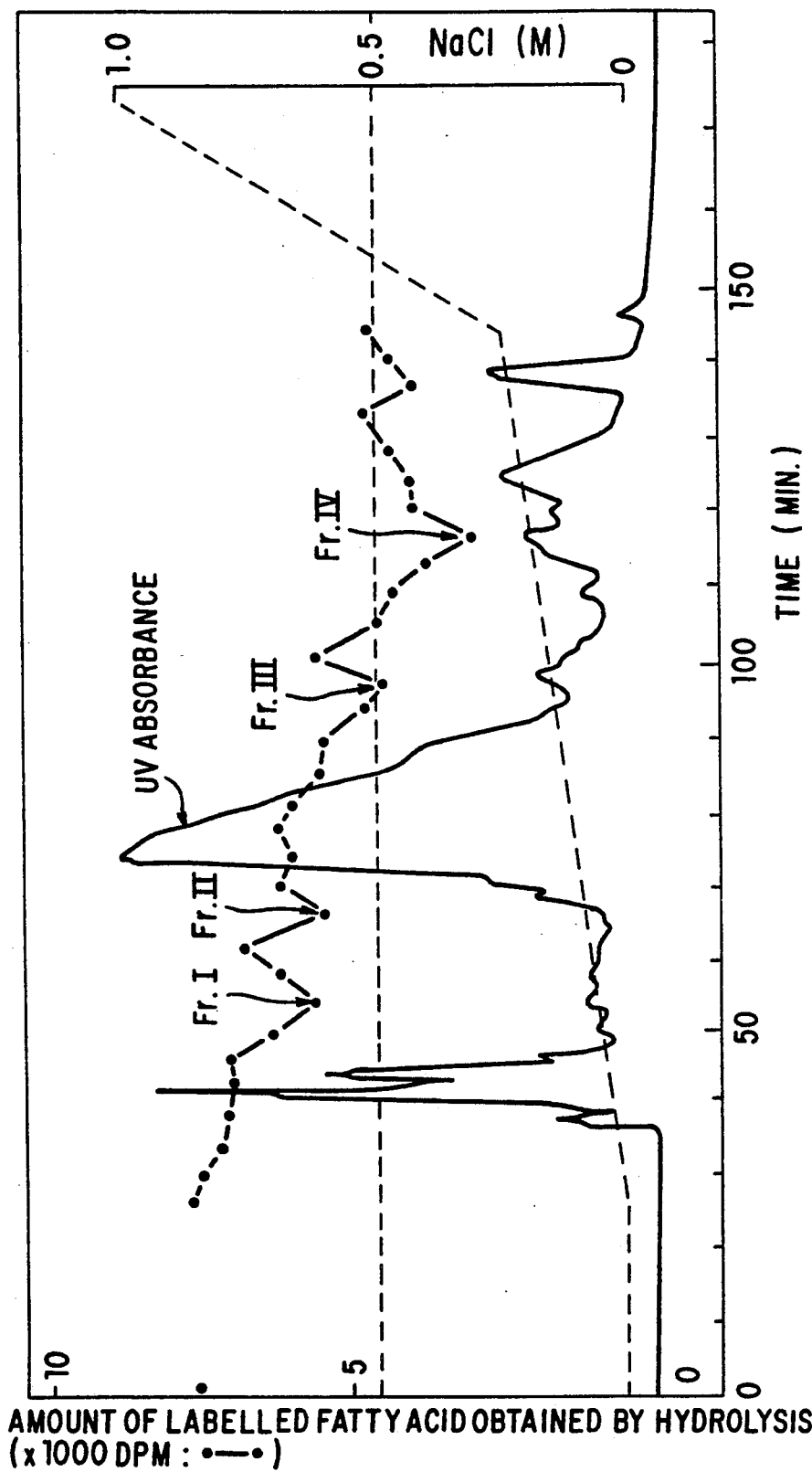
FIG. 1 shows an elution pattern of the subject protein obtained by anion-exchange HPLC.

At first, the isolation and purification of the protein according to the present invention will be described.

Since it is a protein which is produced in vivo by administration of steroid, the protein according to the present invention may be induced by direct administration of a steroid, or it can be also induced by bringing a normal cell or an established cell into direct contact with a steroid in vitro. For example, rats were injected subcutaneously with dexamethasone on the back, one and half hour after injection, they were sacrificed with carbon dioxide and the peritoneal cavities were thoroughly rinsed with saline containing heparin and PMSF (phenylmethylsulfonyl fluoride). The lavages were recovered, combined, dialyzed essentially against an ammonium acetate buffer, and lyophilized. About 20 mg of crude frozen sample of rat peritoneal lavage per head were obtained. The subject protein was isolated and purified from the sample thus obtained, for example, by the following process:

The sample was subjected to, for example, anion-exchange HPLC and the activity peaks were obtained by determining the inhibitory activity of inflammatory PLA$_2$ in each fraction using the activity to inhibit inflammatory PLA$_2$ as an index. The activity peaks were found to consist of many proteins respectively, by SDS-polyacrylamide gel electrophoresis (SDS-PAGE). Further, the active fractions were subjected to gel-filtration HPLC, but they were not purified into a single band, although active fractions were obtained in the operation. Then, the fractions were purified with reverse-phase HPLC to give activity peaks. The peaks were found to be a single protein by SDS-PAGE. About 100 ng of inflammatory PLA$_2$ inhibitory proteins were obtained from some 200 mg of the sample.

As mentioned above, the isolation of a protein from peritoneal cavities of rats induced with a steroid and the purification of the protein having the inflammatory PLA$_2$ inhibitory activity have been explained, but the origin and the preparation of the protein are not limited to them at all in the present invention. It may be extracted from human and other animals than rat or produced from microorganisms or mammalian cells through a biotechnological technique. They will be involved in the present invention, as long as they are proteins having inflammatory PLA$_2$ inhibitory activity.

The methods of testing and determination employed in this invention are as follows:

(1) Method for determinating inflammatory PLA$_2$ inhibitory activity

The inflammatory PLA$_2$ isolated from peritoneal exudate of a rat induced with casein was used and phosphatidyl ethanolamine labeled with $^{14}C$ which had been extracted from E. coli into which $^{14}C$ acetic acid was taken was used as a substrate. The reaction system of the standard was incubated at 37° C. for 10 minutes, after 130 μl of a sample or the control (a buffer solution) were mixed with 50 μl of 0.5 M Tris-HCl (pH 9.0) and 25 μl of 40 mM CaCl$_2$ and 25 μl of the substrate (400 dpm/n mol. 2 mM), finally with 20 μl of inflammatory PLA$_2$ (0.1 ng/μl, 80 Units/mg protein). Then, the reactions were stopped with Dole's reagent. The labeled fatty acid formed by hydrolysis of the phosphatidyl ethanolamine was extracted with heptane and determined with the liquid scintillation counter. The proportion to the control in % was defined as the inhibition rate of the inflammatory PLA$_2$.

(2) SDS-polyacrylamide gel electrophoresis

A part of the samples fractionated by a variety of chromatographic techniques was heated at 100° C. for 10 minutes in the presence of 1% SDS and 2-mercaptoethanol. Then, the sample was applied to 12.5% polyacrylamide gel and subjected to electrophoresis at 15 mA for an hour and half. After electrophoresis, the sample was stained with the silver stain kit (Bio-Rad ®)

(3) Determination of the primary structure of protein

The structure was determined using a gas phase protein sequencer (manufactured by Applied Biosystem, model 470 A). Namely, 10 μg of the isolated and purified sample was dissolved in 30 μl of 1% SDS and applied to the gas phase protein sequencer. The PTH (phenylthiohydantoin) amino acid derivatives formed by automatic Edman's degradation were analyzed in the form of a free amino acid with HPLC respectively.

The present invention will be described in detail by the following examples:

EXAMPLE 1

(1) Preparation of freeze-dried samples of rat peritoneal lavages

Fifty male, 8-week-old SD rats were injected subcutaneously on the back with 1.5 mg/kg of dexamethasone and sacrificed with carbon dioxide one hour and half later. The peritoneal cavities were rinsed thoroughly with 12 ml, per rat, of saline containing 2 units/ml heparin and 50 μM PMSF (phenylmethylsulphonylfluoride) and some 500 ml of lavages were collected. The lavages were dialyzed twice against 10 mM ammonium acetate buffer (pH 7.4) in amount of 40 times and lyophilized to give about 940 mg of a freeze-dried sample of rat peritoneal lavages.

Isolation and purification of subject protein by anion-exchange HPLC

While being cooled with ice, 200 mg of a freeze-dried sample of rat peritoneal lavage were dissolved in 50 ml of 20 mM tris-HCl (pH 8.0). After the solution was filtered through a 0.45 μm membrane filter, the filtrate was directly applied to a column (of TSK GE1 DEAE-SPW) using an sp 8750 HPLC pump. The adsorbed sample was eluted at a flow rate of 2.5 ml/min. with an NaCl linear gradient as shown with a broken line in FIG. 1. In FIG. 1, a solid line indicates the amount of proteins monitored by absorbance at UV 280 nm and a strong inflammatory PLA$_2$ inhibitory activity was detected in Fr. I through Fr. IV. Each fraction was found to be a mixture of proteins different in molecular weight by SDS-PAGE. FIG. 1 shows the amount of labeled fatty acid determined by the method for determining inflammatory PLA$_2$ inhibitory activity.

Figure 2:
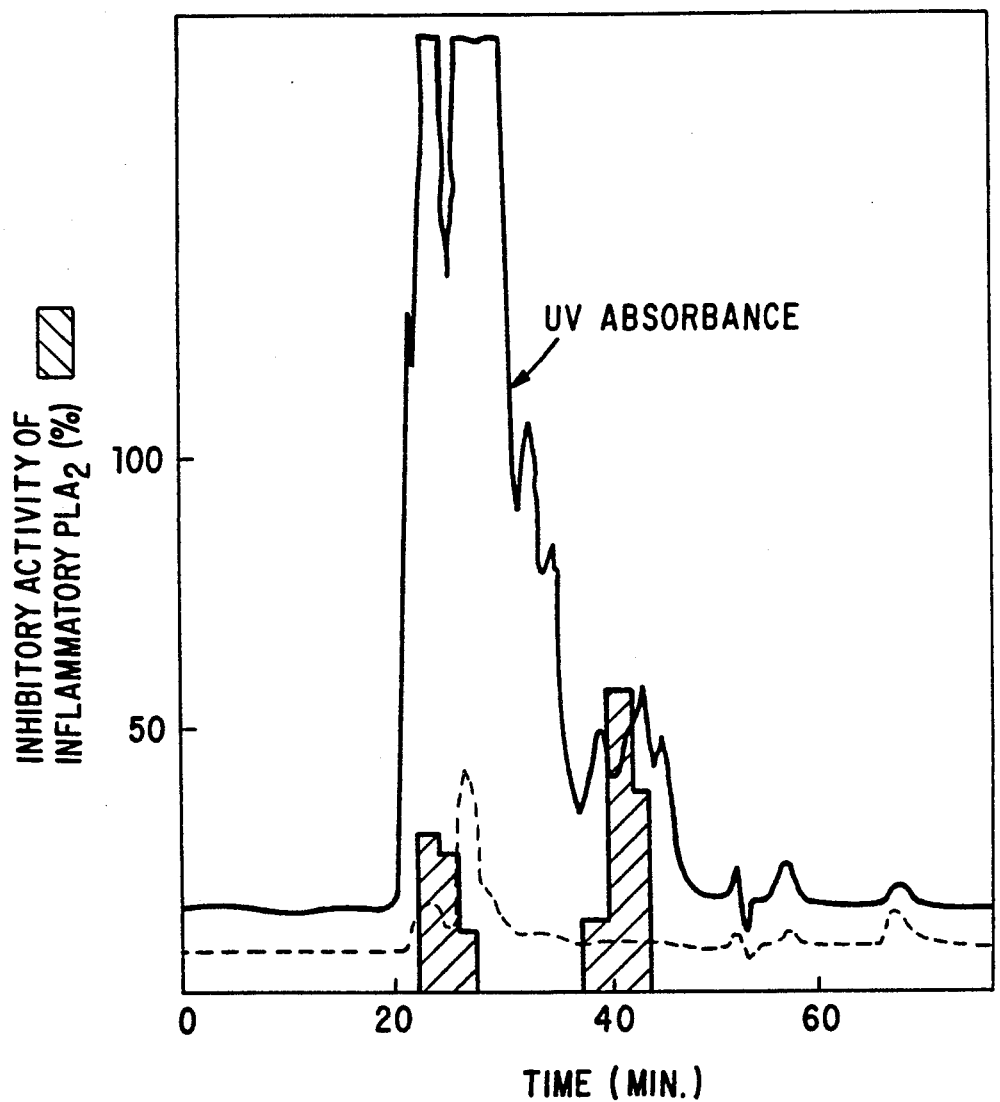
FIG. 2 shows an elution pattern of the subject protein obtained by gel filtration HPLC.

(3) Isolation and purification of the subject protein by gel filtration HPLC Further, the inflammatory PLA$_2$ inhibitory fraction (Fr. IV) was concentrated by ultrafiltration (Centricut 10×3,000 G) in order to purify the fraction. About 0.7 ml of the concentrate was applied to a gel-filtration column (TSK Gel G 3000 SW) equilibrated with 0.1 M Tris-HCl and 1.0 M NaCl at pH 7.7 and eluted at a flow rate of 0.5 ml/min. Two peaks of inflammatory PLA$_2$ inhibitory activity were obtained (the areas painted with oblique lines in FIG. 2). The fractions eluted in the retention time of 37 to 44 minutes were further purified.

Figure 3:
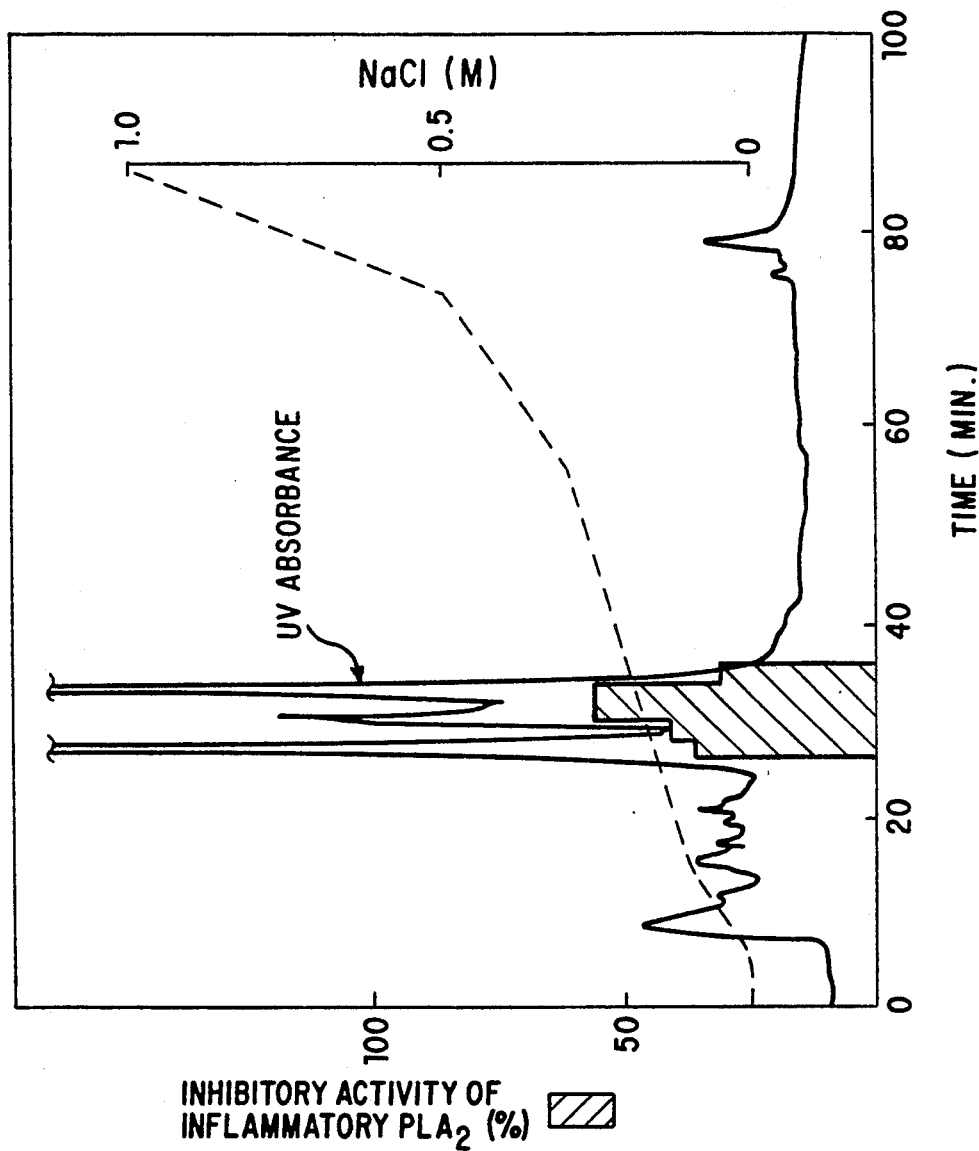
FIG. 3 shows an elution pattern of the subject protein obtained by anion-exchange HPLC.

(4) Isolation and purification of the subject protein by anion-exchange HPLC with an analytical column The fractions which were eluted from the gel filtration column in the retention time of about 40 minutes were collected, dialyzed against 25 mM Tris-HCl (pH 7.7) buffer and applied to an anion-exchange column (TSK Gel DEAE-5 pW) equilibrated with the buffer. The subject protein was separated at a flow rate of 1.0 ml/min with an NaCl linear gradient. The inflammatory PLA$_2$ inhibitory activity was seen in the fractions of 26–36 minute retention time (the area painted with oblique lines in FIG. 3).

(5) Isolation and purification of the subject protein by reverse phase HPLC

Figure 4:
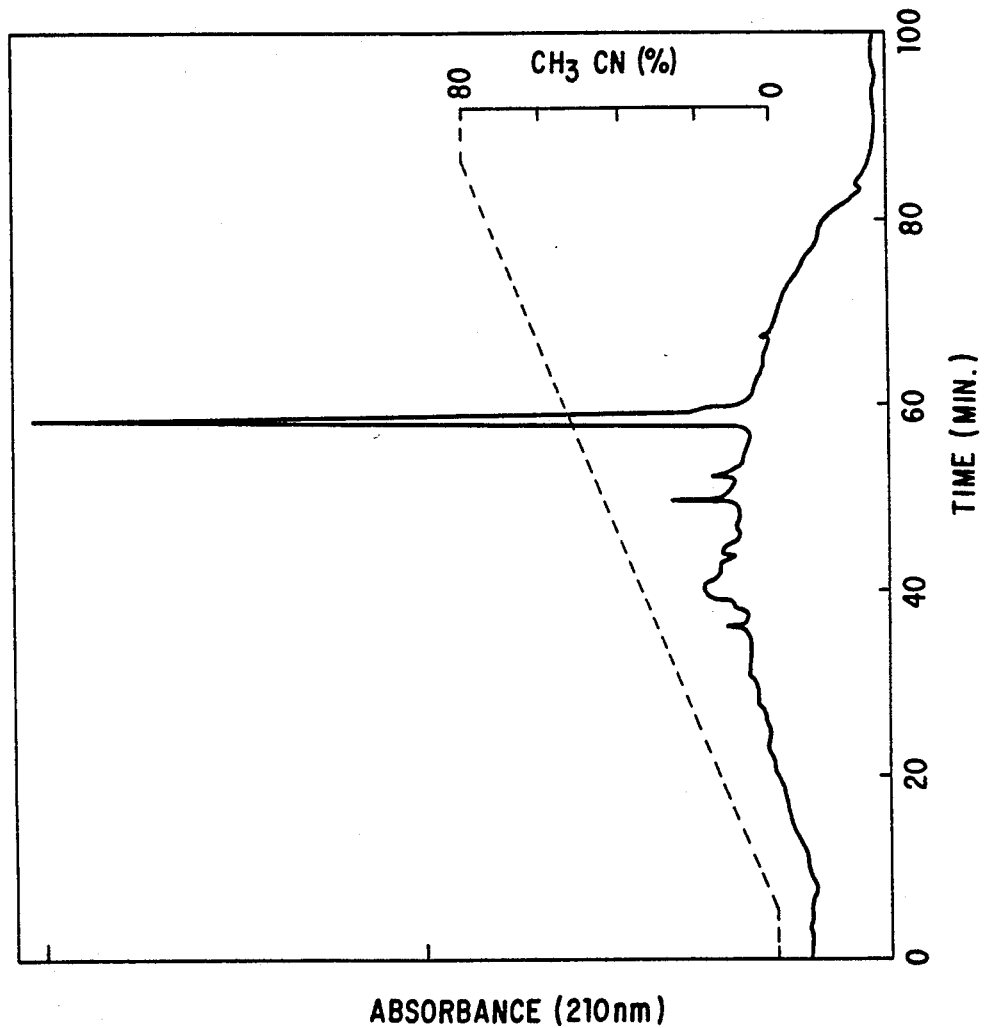
FIG. 4 shows an elution pattern of the subject protein (40 K) obtained by reverse-phase HPLC.
Figure 5:
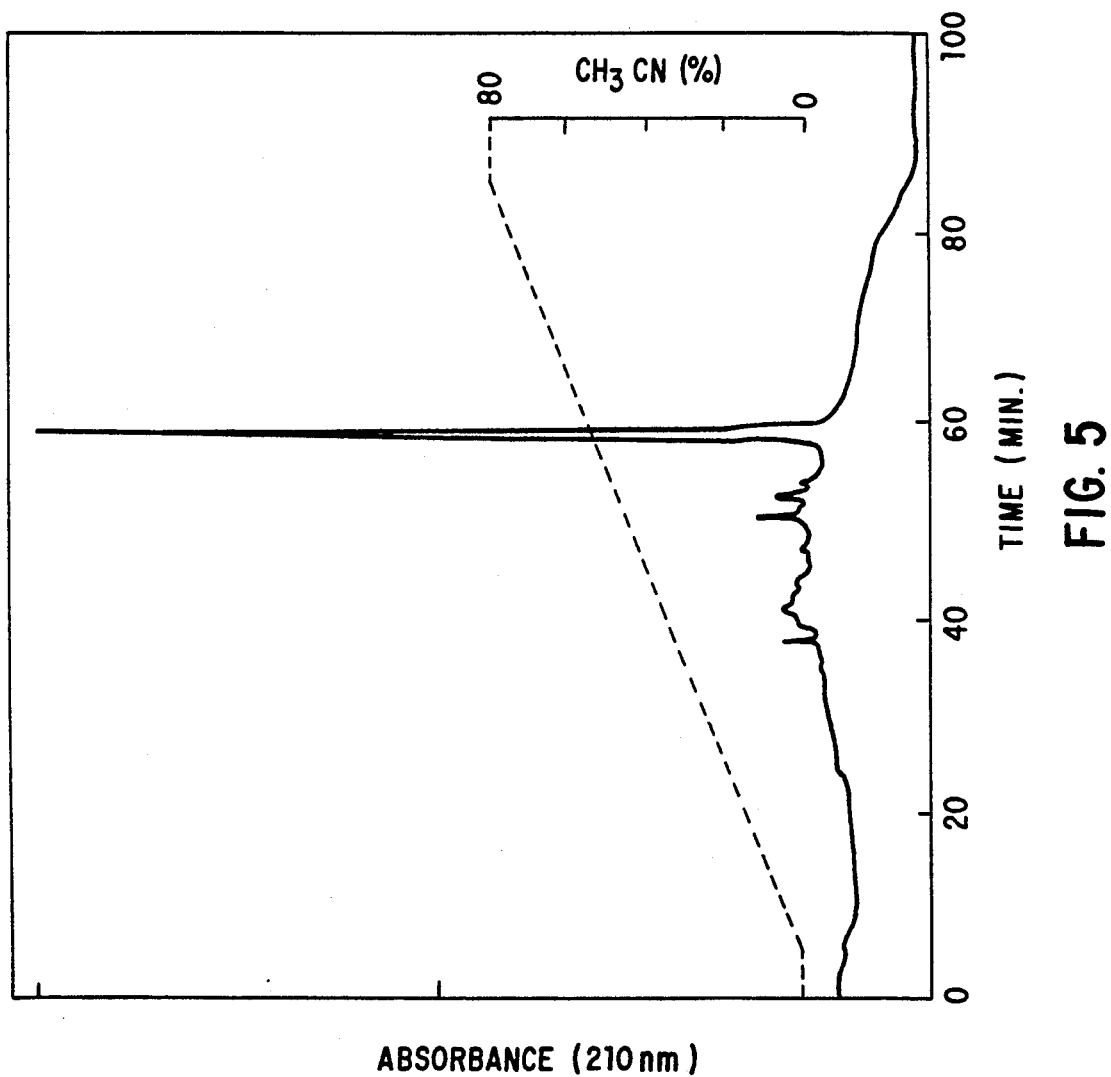
FIG. 5 shows an elution pattern of the subject protein (35 K) obtained by reverse-phase HPLC.

The fractions with inflammatory PLA$_2$ inhibitory activity, fractionated by analytical anion-exchange HPLC, were found, by SDS-PAGE, to mainly consist of 40 K and 35 K. Thus, they were subjected to reverse phase HPLC respectively, so that they were purified into a single protein. The active peaks in FIG. 3 were applied to a column (Bio-Rad Hi-pore RP-304) equibrated with 0.1% TFA respectively. The 40 K protein was eluted at a flow rate of 1.0 ml/min with an acetonitrile linear gradient as shown with a broken line in FIG. 4. The fractions whose absorbance was detected at UV 280 nm, were dialyzed against 25 mM Tris-HCl (pH 9.0) and had their inflammatory PLA$_2$ inhibitory activity determined. As a result, a remarkable inhibitory activity was detected in the single fraction of 59 minute retention time. This fraction was found to be a single protein of about 35,000 molecular weight by electrophoresis.

EXAMPLE 2

The following experiment was carried out in order to known the action mode of the 35 K protein to inhibit inflammatory $PLA_2$:

The concentrations of the enzyme and the inhibitory protein were kept constant and the reaction velocity was measured as the substrate concentration was varied. The results are shown in FIG. 6 by plotting the reciprocals (the open square plots show the enzyme reactions in the inhibitory protein-free system, while the closed square plots, the enzyme reactions in the inhibitory protein-containing system).

Figure 6:
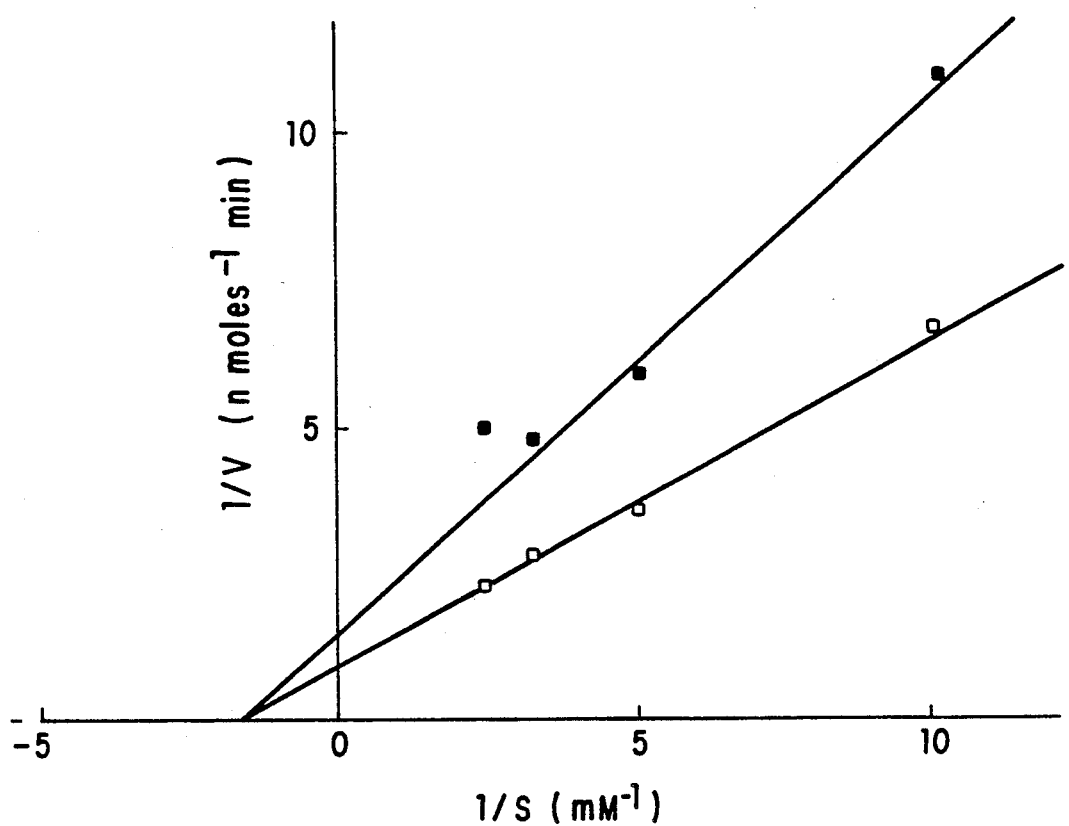
FIG. 6 shows kinetic data of the subject inhibitor protein.

From FIG. 6, it was concluded that the inhibitory mode of the protein is noncompetetive (the substrate and the inhibitory substance act noncompetetively) and the inhibition constant was calculated at $4.5 \times 10^{-8}$ M.

EXAMPLE 3

The primary structure of proteins was partially determined on the samples which were isolated and purified in Example 1. The 40 K protein was found to have the amino acid sequence, although the N-terminal amino acid were not identified, either Glu or Asp, consisting of Asp-Val-Pro-Ala-Ala-Asp-Leu-Ser-Asp- from the second amino acid.

The primary sequence of the 35 K protein was, although the N-terminal amino acid was not identified either Gly or Asp, Glu-Arg-Leu-Lys-His-Leu-Ile-Val from the second amino acid.

Utilization possibility in Industry

The present invention relates to protein having inflammatory $PLA_2$ inhibitory activity. Accordingly, the protein can be utilized as an anti-inflammatory or immunosuppressive for treating a variety of inflammatory diseases and allergic diseases such as rheumatoid arthritis, lupus erythematosus or bronchial asthma by inhibiting inflammatory $PLA_2$ which accelerates the release of inflammatory mediators from arachidonic acid, when inflammation occurs.

We claim:

1. A substantially pure protein which inhibits inflammatory phospholipase $A_2$, wherein said inflammatory phospholipase $A_2$ is isolated from peritoneal exudate of a rat induced with casein, and wherein said protein is isolated and purified from the peritoneal cavity of a rat after administration of a glucocorticoid to said rat, wherein said protein has a molecular weight of about 40 K, and an N-terminal amino acid sequence as follows:

$$\underset{2}{Asp}-Val-Pro-\underset{5}{Ala}-Ala-Asp-Leu-Ser-\underset{10}{Asp}-.$$

2. A substantially pure protein which inhibits inflammatory phospholipase $A_2$, wherein said inflammatory phospholipase $A_2$ is isolated from peritoneal exudate of a rat induced with casein, and wherein said protein is isolated and purified from the peritoneal cavity of a rat after administration of a glucocorticoid to said rat, wherein said protein has a molecular weight of 35 K and an N-terminal amino acid sequence as follows:

$$\underset{2}{Glu}-Arg-Leu-\underset{5}{Lys}-His-Leu-Ile-Val-$$

* * * * *